(12) United States Patent
Shionoya et al.

(10) Patent No.: US 6,506,388 B1
(45) Date of Patent: Jan. 14, 2003

(54) IMMUNOMODULATOR, IMMUNOMODULATOR FOOD

(75) Inventors: Hiroshi Shionoya, Saitama (JP); Mizuo Yajima, Tokyo (JP); Sadaichi Iwashita, Fukuoka (JP)

(73) Assignees: Asama Chemical Co., Ltd., Tokyo (JP); Muromachi Kagaku Kogyo Kaisha, Ltd., Tokyo (JP); Muromachi Chemical Co., Ltd., Fukuoka (JP)

( * ) Notice: Subject to any disclaimer, the term of this patent is extended or adjusted under 35 U.S.C. 154(b) by 0 days.

(21) Appl. No.: 09/441,162

(22) Filed: Nov. 15, 1999

(30) Foreign Application Priority Data

Nov. 20, 1998 (JP) .......................... 10-330395
Dec. 8, 1998 (JP) .......................... 10-348065

(51) Int. Cl.[7] .................. A61K 39/05; A61K 39/02; A61K 45/00; A61K 47/00; A61K 39/00
(52) U.S. Cl. ............... 424/238.1; 424/234.1; 424/184.1; 424/245.1; 424/282.1; 424/9.2; 424/439
(58) Field of Search ................ 514/2, 23; 424/9.2, 424/464, 184.1, 234.1, 238.1, 245.1, 282.1, 439, 442; 426/72, 71, 658, 805

(56) References Cited

U.S. PATENT DOCUMENTS

| | | | | |
|---|---|---|---|---|
| 4,360,510 A | * | 11/1982 | Proctor ..................... | 424/1.5 |
| 4,479,935 A | | 10/1984 | Metianu et al. ............ | 424/92 |
| 4,515,891 A | * | 5/1985 | Yokogawa et al. ......... | 435/69 |

FOREIGN PATENT DOCUMENTS

| | | |
|---|---|---|
| DE | 3301997 A1 | 8/1993 |
| EP | 0 024 941 A2 | 3/1981 |
| EP | 0 416 892 A1 | 3/1991 |
| EP | 0512857 A2 * | 11/1992 |
| GB | 002133032 | 4/1977 |
| GB | 002133031 | 1/1983 |
| JP | 48088225 * | 11/1973 |
| WO | WO 98/39025 | 9/1998 |

OTHER PUBLICATIONS

Gialdroni–Grassi et al. Int. Archs. Allergy Appl. Immn. 76: Suppl. 119–127, 1985.*
Kotani et al. Z. Immunitatsforsch. Exp. Klin. Immunol. (West Germany) 149: 302–319, abstract, 1975.*
The Webster's II New Riverside University Dictionary, p. 933, 1984.*
Henocq et al. Rev. Inst. Med. Trop. Sao Paulo 26: 105–109, 1984.*
Levy et al. Israel J. Med. Sci. 30: 873–879, abstract, 1994.*
Kotani et al. Biken J. 20: 87–90, abstract, 1977.*
Origin and Fate of IgE–Bearing Lymphocytes, by Durkin et al, The Journal of Immunology, Sep. 15, 1989, pp. 1777–1783.
Antitumor Glycopeptides from *Lactobacillus bulgaricus* Cell Wall, by I.G. Bogdanov et al, Febs Letters, vol. 57, No. 3, pp. 259–261, Oct. 1975.
Effect of Oral Administration of Lysozyme or Digested Bacterial Cell Walls on Immunostimulation in Guinea Pigs, by Yzuburo Namba et al, Infection and Immunity, vol. 31, No. 2, pp. 580–583, Feb. 1981.
Biological Activities of Bacterial Cell Wall Peptidoglycans and Their Subunits, with Special Reference to the Immunoadjuvant Actions, by S. Kotani, Department of Microbiology, Osaka University Dental School, pp. 1081–1107, 1976 (with Summarized English Translation Attached).

* cited by examiner

*Primary Examiner*—S. Devi
(74) *Attorney, Agent, or Firm*—Flynn, Thiel, Boutell & Tanis, P.C.

(57) ABSTRACT

An immunomodulator having suppressive activity on IgE antibody production is provided and contains bacterial cells, or their decomposition materials. It can be taken as a food. Bacterial cells such as Corynebacterium, Brevibacterium, Microbacterium, or bacterial cells of mutant strains of these bacteria, or decomposition products of these bacteria are used.

2 Claims, No Drawings

IMMUNOMODULATOR, IMMUNOMODULATOR FOOD

FIELD OF THE INVENTION

The present invention relates to a decomposition product of bacterial cell walls, an immunomodulator, consisting of bacterial cells or their decomposition materials which can suppress selectively IgE antibody production, and to provide their production methods and foods containing them.

RELATED ART

Immediate type allergies or atopies, such as pollen allergy, asthma, atopic dermatitis, food allergy, are known to be mediated by antibody of IgE isotype immunoglobulin. Symptoms of atopy are elicited when the IgE antibodies react to antigen, resulting in release of various physiologically active substances such as histamine, serotonin, leucotrienes and others.

For the prevention and treatment of immediate type allergies, drugs generally used today are those which are antagonistic to the mediators, for instance, antihistaminics, drugs which inhibit release of mediates from mast cells, and corticosteroids which inhibit activation of various immunocytes resulting in inhibition of cytokine production.

Since the antibody which mediates an immediate allergy is an IgE antibody, an agent which suppress IgE antibody production can be thought to be effective for the treatment of immediate type allergies. However, there are no effective drugs which suppress only IgE isotype antibody without suppressing other isotypes such as IgG, IgA so on,which are important for body defense mechanisms to various infectious diseases.

SUMMARY OF THE INVENTION

Accordingly, an object of the present invention is to provide an immunomodulator having suppressive activity on IgE production without any suppressive effect on other isotypes of antibody.

As a result of extensive investigation in order to solve the above-mentioned problem, the present investigators have unexpectedly found firstly that bacterial cells of Corynebacterium, Brevibacterium, and Microbacterium species, and mutant strains derived from the species are able to suppress selectively IgE type antibody production by oral administration of these bacterial cells without any suppressive effect on the production of other isotypes, even if enhancing these antibody production, and secondly that a decomposition product of above mentioned bacteria by enzymatic treatment and such, has more potent immunomodulative activity than that of the bacterial cells by themselves. These findings have led to the completion of the present invention.

That is, the present invention is to provide an immunomodulator, an immunomodulator food, immunomodulator drink containing bacterial cells belonging to Corynebacterium, Brevibacterium, and Microbacterium species, and mutant strains derived from the species, and a decomposition material of the above mentioned bacteria by enzymatic treatment and such.

The invention provides a method of modulating the immunological function by administering orally a pharmacologically effective amount of bacterial cells or their decomposition materials to a human being.

The invention provides a bacterial cell wall decomposition product (or decomposition material) having an immunomodulative activity, which is produced by dissolving the cell wall of at least one selected from the group consisting of bacteria belonging to Corynebacterium genera, Brevibacterium genera and Microbacterium genera and mutant strains of these bacteria.

The invention provides a process for manufacturing the above-shown bacterial cell wall decomposition product, which comprises dissolving the cell wall of at least one selected from the group consisting of bacteria belonging to Corynebacterium genera, Brevibacterium genera and Microbacterium genera and mutant strains of these bacteria.

It is preferable to the process to dissolve the cell walls with one of glucosidase and endopeptidase in the medium of an isotonic solution, separate the protoplast generated by the enzymatic digestion of the bacterial cells from the medium, and furthermore enzymatically treat the dissolved material of the bacterial cells with the other of the endopeptidase and glucosidase.

It is preferable to dissolve the cell walls with one of glucosidase and endopeptidase in the medium of an isotonic solution (biological saline), centrifuge the solution to obtain the supernatant and enzymatically treat the supernatant with the other of the endopeptidase and glucosidase.

The decomposition production of the invention may be obtained when at least 30% or 29% of the bacterial cells have been decomposed. This decomposition extent can be observed in terms of determination of dissolved hexosamine or glucosamine, which is present in the supernatant. Alternatively, it can be observed in terms of optical density of the bacterial suspension. The invention may reach at least 25% of optical density.

The invention provides an immunomodulator food or drink containing the bacterial cell wall decomposition product of the invention.

The invention provides a method of treating or preventing allergy, which comprises administering a pharmacologically effective amount of the decomposition product of the invention to a person suffering from allergy, and use of the decomposition product for manufacturing immunomodulator.

The invention relates to use of bacteria belonging to Corynebacterium genera, Brevibacterium genera and Microbacterium genera and mutant strains of these bacteria. That is, the invention provides a method of treating or preventing allergy, which comprises administering a pharmacologically effective amount of the bacteria to a person suffering from allergy; use of the bacteria for manufacturing immunomodulator; an Immunomodulator food or drink containing the bacteria; and a method of effecting immunomodulation, which comprises administering a pharmacologically effective amount of the bacteria to a person suffering from immunodeficiency.

It is preferred to the production of the decomposition product that the bacterial cell wall is digested with glucosidase and/or endopeptidase; a bacterium of Corynebacterium genus is *Corynebacterium glutamicum* or *Corynebacterium herculis*; a bacterium of Brevibacterium genus is *Brevibacterium flavum*; a bacterium of Microbacterium genus is *Microbacterium ammoniaphilum*; the glycosidase is egg white lysozyme or N-acetylmuramidase SG; the decomposition is performed by induction of lysogenic bacteriophage; the decomposition is performed by autolysis; the endopeptidase is bromelain; or the endopeptidase is one selected from the group consisting of seratiopeptidase, protease produced by Streptomyces griseus (K-1 strain), protease produced by Bacillus subtilis, Seaproze S produced by *Armill-* aria mellea (Naratake in Japanese), trypsin, Achromobacter protease I and *Grifola frondosa* (Maitake in Japanese) metaloendopeptidase.

It is preferable that the immunomodulative bacterial cells are products produced by culturing cells of strains belonging to Corynebacterium, Brevibacterium, and Microbacterium species, and mutant strains derived from the species, heating the culture to kill the cells, harvesting the killed cells and dried. As for products of immunomodulative decomposition materials made of the above-mentioned bacteria, cultured cells are decomposed by autolysis, induction of lysogenic bacteriophage, and enzymatic treatment using cell wall digesting enzymes.

In the invention, decomposition material is defined by a generation of soluble hexosamine of at least 30% of the total bacterial hexosamine.

DETAILED DESCRIPTION OF THE INVENTION

An immuno-adjuvant is called for as the substances which enhances antibody formation by injecting them mixed with an antigen to animals. Killed bacterial cells of *Mycobacterium tuberculosis* have been known to have immuno-adjuvant activity. Results of study for clarifying an effective component of the adjuvant activity revealed that the smallest component was muramyl-L-alanyl-D-isoglutamine (MDP), a component of peptidoglycan of bacterial cell wall. The existence of MDP is also known in all the bacterial cells other than bacteria of *Mycobacterium tuberculosis*, including pathogenic and also non-pathogenic bacteria, irrespective to classification by gram-positive and gram-negative staining. In fact, bacterial cell wall fractions containing MDP showed adjuvant activity in almost all bacteria studied (Kotani, S. Seikagaku 48, 1081–1107 1976 in Japanese).

A mucopeptide layer of bacterial cell wall is consisted of long glucosidase chains polymerized at β-1,4 linkage of N-acetylglucosamine and muramic acid, and of peptide linkage which links calboxylic residue of muramic acid with alanine or L-glycine, D-glutamic acid, L-lysine or mesodiaminopimeritc acid, D-alanine in this turn. The last D-alanine makes peptide bond with a carboxic residue of another D-glutaminc acid, lysine and mesodiaminopimeric acid which is in the peptide chain originated from a neighboring glucoside chain. Number of amino acids in the peptide which links two neighboring glucoside chain are, somewhat different dependent on species of bacteria, 6 to 7 amino acids. Supposing that many glucoside chains arranged in parallel with each other are the warps, the peptide chains which bind the glucoside chains to each other are the wefts, therefore, both the wefts and the warps make a net-like structure and named peptidoglycan. The peptidoglycan surrounds cytoplasm of the bacterial cell and makes strong wall which protect the bacterial cell from damage by physical change of osmotic pressure.

The enzymes which solubilize the bacterial cell walls belong to the hydrolyze enzyme. Depending on their actin mechanisms, they are divided to three categories. One is glycosidase which hydrolyze carbohydrate linkage (for an instance egg-white lysozyme), others are endopeptidase which hydrolyze peptide bonds of peptidoglycan and amidase which hydrolyze a bond between muramic acid and amino acid.

Accordingly, MDP containing components are solubilized from bacterial cell wall by above-mentioned hydrolyze enzymes excluding amidase.

Being based on these background, various researches have been performed for the purpose of potentiation of immune status of the host. As the results, it has been reported studies on the resistance to tumor (Bogdanov I. G. et al. Antitumor glycopeptide from *Lactobacillus bulgaricus* cell wall FEBS LETT: 57(3)259–261 1975), activation of macrophage function and cellular immunity concerning anti-infectious immunity, and enhanced production of IgG antibody that plays important role for the resistance to bacterial and viral infections (Nammba Y et al. Effect of oral administration of lysozyme or digested cell wall on immunostimulation in guinea pigs. Infect Immun 31: 580–583 1981). As for relationships between chemical structure and biological activity, bacterial cell wall and its enzymatic digested material have been studied (Kotani, S. Seikagaku 48, 1081–1107 1976 in Japanese). However, no findings have been reported today as for production of IgE antibody which includes allergic disease such as atopy.

In the present invention, the bacteria are not necessarily special bacteria. However, in view of the safety and the utilization of waste material, amino acid-producing bacteria, for example, *Corynebacterium glutamicum, Corynebacterium herculis, Corynebacterium fermentum, Brevibacterium flavum* and *Microbacterium ammoniaphilum* can be mentioned.

The present inventors investigated effect of above-mentioned bacterial cells, a mutant strain of these bacteria, and enzymatically digested materials of these bacterial cells on IgE antibody production by oral administration, and have found that each bacterium suppressed IgE antibody production by administering heat-killed bacteria, enzymatically digested materials of the bacteria containing MDP, and that the IgE production suppressing activity of bacterial cells was potentiated by digesting the cells with cell-wall digesting enzymes.

Culture of bacteria belonging to genera of Corynebacterium, Brevibacterium and Microbacterium can be made by a known method in an appropriate medium. Any form of bacterial cell preparations can be used as a starting material such as the culture itself, centrifuged cells, freeze-dried cells, heat-killed cells and spray-dried cells for the purpose of production of the final raw products. Heat-killed cells or spray dried cells can be used as the IgE production immunomodulative material having suppressive effect on IgE production.

Production of the immunomodulative decomposition material starting from bacterial cell preparations is performed by solubilizing bacterial cell wall by means of using cell wall digesting enzymes, induction of lysogenic bacteriophage and autolysis using endogenous autolytic enzymes.

Of the methods mentioned above, an efficient method of decomposition of bacterial cell walls is the method using glycosidase and/or protease of endopeptidase type. The present invention revealed that the decomposition material produced by use of both of glycosidase and proteinase had more potent immunomodulative activity than that produced by use of either one of the two enzymes. Comparing the activity produced by two kinds of the enzymes, glycosidase is preferential. As an example of glycosidase, egg-white lysozyme, bacterial lysozyme and N-acetylmulamidase SG are mentioned. Of them, egg-white lysozyme is recommended from a stand point of safety of the product because this enzyme is used as a food additive.

As an example of the endopeptidase, bromelain, seratiopeptidase, protease produced by *Streptomyces griseus* K-1 (Pronase®), protease produced by *Bacillus subtilis* (Nagase®), Seaprose S produced by *Armillaria mellea* (Naratake in Japanese), Acromobacter protease 1 (lysylendopeptidase) and metalloendopeptidase produced by *Grifola frondosa* (Maitake in Japanese) can be mentioned. Of these, bromelain is recommended from a stand point of safety of the product because this enzyme is used as a food additive.

Sensitivity of bacterial cells to glycosidase digestion differs depending on the bacterial strain. The sensitivity can be enhanced by addition of penicillin or glycine in culture medium as described in Examples 1 and 2. Enzyme treatment is conducted under nearly optimal pH of the respective enzymes. The treatment by glycosidase and endopeptidase is performed under nearly neutral pH, i.e., pH 5 to 8. An amount of enzyme added to 1 gm of dry bacterial cells is 0.01 to 10 mg. Temperature of enzyme treatment can be conducted at room temperature to 70° C. DNase and RNase at concentrations of 10 to 500 ug/ml can be added to the reaction mixture to reduce viscosity of the mixture.

Decomposition of bacterial cell by an induction of lysogenic bacteriophage can be done by UV irradiation of each of bacterial culture of Corynebacterium, Brevibacterium and Microbacterium. Decomposition of bacterial cell by autolysis can be performed by incubation of bacterial cell suspended in purified water at about 50° C. for 1 to 3 days.

A definite method for production of the immunomodulative decomposed material of the present invention is, for example, the following. *Corynebacterium glutamicum* is cultured in appropriate medium. The culture is centrifuged to collect bacterial cells. The cells are suspended in physiological isotonic solution such as physiological saline, and then either of glycosidase such as egg-white lysozyme or endopeptidase such as bromelain is added to the suspension to solubilize the bacterial cell wall. Bacterial cytoplasmic membrane and cytoplasm surrounded by the cytoplasmic membrane exist as protoplasts by this stage of enzyme treatment. The protoplast is sedimented by centrifugation and discarded. Then, the supernatant, which contains MDP containing cell wall components, is treated with another enzyme, i.e., endopeptidase (if enzyme used at the first step is glycosidase) such as bromeline or glycosidase (if enzyme used at the first step is endopeptidase) such as egg white lysozyme.

A preferable method is the following. At first, the bacterial cell wall is solubilized by treatment with glycosidase and protoplast is sedimented and discarded and then endopeptidase treatment of the supernatant solution is conducted. Elimination of the protoplast effectively purify the active decomposed material of the present invention as in the Examples. The immunomodulative active decomposition material can be precipitated by adding ethanol or acetone to the supernatant.

Other method of preparation of the present invention is the following. *Corynebacterium glutamicum* is cultured and the bacterial cells are harvested and suspended in purified water. Then, at first, glycosidase is added to the suspension and incubated to lyse cell wall and then endopeptidase is added to the suspension and incubated.

The process of,decomposition of bacterial cells is measured by the estimation of optical density of bacterial suspension at wavelengths of 600 to 660 nm as described in Example 7 or by hexosamine determination of supernatant solution after centrifugation of bacterial suspension as described in Example 4. Hexosamine determination can be conducted by ordinary methods such as the Elson-Morgan Method and the Reissig, Strominger and Leloir Method.

An enhanced activity on immunomodulation owing to decomposition of bacterial cells is observed when at least 30% of bacterial cells have been decomposed in terms of dissolved hexosamine determination. Alternatively, at least 25% reduction of optical density of the bacterial suspension is preferably found for this purpose as in Example 4.

A standard oral daily dose of the immunomodulative bacterial cells and their decomposition material of the present invention is between 0.2 and 2 g. The desirable dose is about 1 g equivalent to killed dry cells.

When the immunomodulative decomposition material of the present invention is applied as a main agent, it can orally be used in powder, tablets, dispersion, capsules, confectionery, bread, noodles, drinks or the like. These products can be made by ordinary production methods.

EXAMPLES

The present invention is illustrated more specifically be giving the following examples. By the way, in Examples, % and parts are both on the weight basis.

Example 1

Decomposition Material by Enzyme Treatment

*Corynebacterium glutamicum* IAM 12435 was inoculated into an L-shaped tube containing 10 ml of nutrient broth, and incubated while being shaken at 30° C. for 7 hours. One ml of this culture was inoculated in each of 10 conical flasks (Erlenmeyer flask) having a capacity of 500 ml and containing 100 ml of a medium of Miura et al. (Hakko Kogaku Zasshi, Vol. 41, No. 5, pp. 275–281, 1963), and incubated while being shaken at 30° C. for 24 hours. Penicillin G was added at a concentration of 0.2 U/ml in the logarithmic phase of the culture. The cells were harvested by centrifugation to obtain approximately 5 g of wet cells. The wet cells were washed by centrifugation once with physiological saline. Then, 1 liter of physiological saline was added to the sediment to suspend the cells. Five mg of egg-white lysozyme was added thereto while being stirred. After the stirring at 37° C. for one hour, 5 mg of seratiopeptidase was added and incubated at 37° C. for one hour under stirring. Thus, the decomposed material was prepared. This was heated at 80° C. for 30 min and freeze-dried. 5 g of dry material was obtained.

Example 2

Decomposition Material by Enzymatic Digestion and Purification

*Corynebacterium glutamicum* IAM 12435 was inoculated into an L-shaped tube containing 10 ml of nutrient broth, and incubated while being shaken at 30° C. for 7 hours. One ml of this culture was inoculated in a conical flask (Erlenmeyer flask) having a capacity of 500 ml and containing 100 ml of nutrient broth and incubated while being shaken at 30° C. for 8 hours. The whole culture in the flask was inoculated into a jar fermenter of inner volume of 2 liter and containing 1.5 liter of Mimura's medium and incubated at 30° C. for 20 hours under aeration. Penicillin G was added at a concentration of 0.2 U/ml in the logarithmic phase of the culture. The cells were harvested by centrifugation to obtain 7.5 g of wet cells. After washing the wet cells with physiological saline by centrifugation, the cells were resuspended with 200 ml of physiological saline and added with 5 mg of egg-white lysozyme while being stirred for one hour at 37° C. Assessment of lysozyme treatment was performed by an estimation of optical density (OD) at 660 nm for the samples obtained before and after the treatment. OD values of 40 fold diluted suspensions before and after egg-white lysozyme treatment were 1.20 and 0.77, respectively. The reduction of optical density is calculated as 35.8%. The incubation mixture was centrifuged at 13000 rpm for 30 min. The sediment containing protoplasts was discarded and the supernatant was obtained. The supernatant was added with 5 mg of seratiopeptidase and incubated at 37° C. for one hour under stirring. Thus, the decomposition material was prepared. This was heated at 80° C. for 30 min, desalted by dialysis and freeze-dried to obtain 0.2 g of dry material.

Example 3

Decomposition Material by Enzymatic Digestion and Purification

The immunomoduiative decomposition material produced according to the method of Example 2 in which 5 mg of bromelaine was used instead of the same amount of seratiopeptidase. Assessment of lysozyme treatment was performed by an estimation of OD at 660 nm for the samples obtained before and after the treatment. OD values of 40 fold diluted suspensions before and after egg-white lysozyme treatment were 1.05 and 0.76, respectively. The reduction of optical density is calculated as 27.6%. Thus, 0.3 g of the dry material was obtained.

Example 4

Decomposition Material by Enzymatic Digestion

One kg of freeze-dried bacterial cells of *Corynebacterium glutamicum* IAM 12435 was suspended with 12 l of physiological saline. Then, 100 ml physiological saline containing 5 g of egg-white lysozyme was added to the suspension. After stirring for 1 hour at 30° C., 200 ml of physiological saline containing 5 g of bromelain was added and incubated at 30° C. for 1 hour under stirring to make the decomposed material of the present invention. The material was spray-dried to obtain 1 kg of the dry material.

Assessment of decomposition was performed by determining solubilized hexosamine from bacterial cells. Two-tenth ml of bacterial suspension was diluted five fold with purified water and centrifuged at 16000 rpm for 10 min and a supernatant solution was separated. Hexosamine contents of the five fold diluted suspension and those in the supernatant solution, before and after lysozyme and bromelain treatment were analyzed by the method of Reissig, Strominger and Leloir method. The results of estimation of each of the bacterial suspension, supernatants before lysozyme treatment and after bromelain treatment were 1820, 0, and 535 µl/ml, respectively. The amount of decomposed bacteria is calculated as 29.4% from 535/1820.

Example 5

Decomposition Material by Enzymatic Digestion

The same process as in Example 4 was repeated, except that freeze-dried bacterial cells of *Corynebacterium glutamicum* ATCC 13032 was used instead of that of *Corynebacterium glutamicum* IAM 12435, to obtain 1 kg of the above-mentioned dry decomposed material.

Example 6

Decomposition Material by Autolysis

One kg of freeze-dried bacterial cells of *Corynebacterium Glutamicum* ATCC 13032 was suspended in 20 l of purified water and the suspension was kept at 50° C. for 24 hours to autqlysis the bacterial cells. The autolysate was spray-dried and 1 kg of the dry decomposed material was obtained.

Example 7

Decomposition Material by Cell Lysis According to Lysogenic Bacteriophage Induction Bacterial cell lysis by inducing lysogenic bacteriophage of Corynebacterium was performed as the following.

*Corynebacterium glutamicum* ATCC 31830 was inoculated into conical flask (Erlenmeyer flask) having a capacity of 500 ml and containing 100 ml of nutrient broth and incubated while being shaken at 30° C. for 24 hours. After harvesting the bacterial cells through centrifugation, the cells were suspended in phosphate buffered physiological saline. Twenty milliliters of the bacterial cell suspension were poured into a Petri dish of 9 cm diameter and exposed to UV light for 20 sec under stirring using 15 W germicidal UV lamp at a distance of 40 cm. After the irradiation, the suspension was added with 20 ml of nutrient broth of 2 fold concentration of an ordinary broth and cultured for 2 hours at 30° C. under shaking. The optical density at 660 nm of the bacterial suspension at the beginning of cultivation was 5.0, and that after 2 hour incubation was 2.2, demonstrating bacterial lysis.

Example 8

Decomposition Material by Enzymatic Digestion

*Corynebacterium glutamicum* ATCC 15354 was inoculated in each of 20 conical flasks containing 100 ml of a nutrient broth, and incubated while being shaken at 30° C. for 18 hours. The cells were harvested by centrifugation to obtain approximately 3 g of wet cells. The wet cells were washed by centrifugation once with physiological saline. Then, 500 ml of physiological saline was added to the sediment to suspend the cells. Four mg of egg-white lysozyme was added thereto while being stirred. After the stirring at 37° C. for 2 hours, 4 mg of seratiopeptidase was added and further incubated at 37° C. for 2 hours under stirring to obtain the decomposition material of the present invention. This was heated at 80° C. for 30 min and freeze-dried to obtain 3 g of the dry material.

Example 9

Suppressive Activities on IgE Production of Heat-killed Cells, Heat-killed and Enzymatically Decomposed Cells and Heat-killed, Enzymatically Decomposed and then Purified Fraction One group consisted of 6 female BALB/c mice of 6 weeks old were fed with feed which contained each of heat-killed bacterial cells of Corynebacterium glutamicum, preparations of the present invention mentioned in Examples 3 and 4. After two weeks of feeding, mice were immunized with 0.1 ml of physiological saline solution containing 10 pg of egg albumin and 1 mg of alum. Then, blood of each mice was taken by retro-orbital puncture 14 days after the immunization and serum was separated. Six sera of each group were pooled and IgE antibody titer of the pooled sera was measured by rat PCA reaction. Briefly, 15 to 20 week old male SD rats were shaved on the back and 0.1 ml of serum previously diluted with physiological saline was intradermally injected into the back of 2 recipient rats under pentobarbital anesthesia. After 24 hours of intradermal injection of sera, one ml of physiological saline solution containing 1 mg of egg-albumin and 10 mg of Evans blue dye was intravenously injected to the rats under pentobarbital anesthesia. Thirty minutes after the intravenous injection, diameters of blue spots appeared on the back of the site of serum injection were measured. The mean diameter more than 5 mm was judged as a positive reaction. An antibody titer was expressed as a reciprocal of serum dilution. Of the two antibody titers obtained from two recipient rats, the higher one was adopted as the antibody titer for each of the pooled sera. The results were shown in Table 1. In the table, Judgement of immunomodulative activity was significant in case there was a difference more than 2 serial dilution between control group and fed group and + was added for the difference of each one serial dilution.

TABLE 1

| Immunomodulator | Dose (%) | Animal group No. | PCA antibody titer | Judgement |
|---|---|---|---|---|
| Control | 0 | 1 | 80 | − |
| Heat killed cell | 0.01 | 2 | 80 | − |
| | 0.1 | 3 | 40 | − |
| | 1 | 4 | 10 | ++ |
| Enzymatically decomposed whole cell (Example 4) | 0.01 | 5 | 40 | − |
| | 0.1 | 6 | 10 | ++ |
| | 1 | 7 | 0 | ++++ |
| Enzymatically decomposed active fraction (Example 3) | 0.001 | 8 | 20 | + |
| | 0.01 | 9 | 10 | ++ |
| | 0.1 | 10 | 0 | ++++ |
| | 1 | 11 | 0 | ++++ |

As shown in Table 1, an administration to mice with heat killed cells or its decomposed materials prior to an antigenic stimulation suppressed IgE antibody production. The results have revealed that the administration had influence on the immunological reactivity of the body or the constitution. The result that the stronger effect was observed by an administration of the decomposed material of Example 4 in comparison with killed cell alone showed that enzymatic treatment of bacterial cells fortified the suppressive activity, furthermore, that the suppressive activity for IgE antibody production was the most potent in groups administered with the decomposition material of Example 3 revealed that the active decomposition material was mainly constituents of bacterial cell wall.

Example 10

Enhancing Activities on IgG Production of Heat-killed Cells, Heat-killed and Enzymatically Decomposed Cells and Heat-killed, Enzymatically Decomposed and then Purified Fraction Effect of immunomodulative decomposition material on IgG antibody production was examined by ELISA of anti-egg-albumin igG anti body estimation in the sera of mice of Example 9. Well-s of micro-plate (96-well flat bottom ELISA plate, Coster, Cambridge, Mass., USA) was added with 50 µl of egg-albumin solution (0.1 mg/ml in 0.05 M carbonate buffer, pH 9.5), and kept at 4° C. overnight. After washing the wells with a solution containing 0.9% NaCl and 0.05% Tween® 20 (polyoxyethylene derivative from sorbitanhyide), 200µl of bovine albumin solution (1 mg/ml BSA in phosphate buffered physiological saline (PBS Nissui Pharmaceutical Co.) was added to the wells and incubated at 37° C. for one hour to block any nonspecific binding. Next, after washing, 50 µl of sera of mice prepared in Example 9, previously diluted with PBS solution containing 10 mg/ml BSA, 0.05% Tween® 20 and 3% NaCl (Solution A) was added to the wells and kept at 37° C. for 1 hour. Then, after washing the wells, the wells were added with 50 µl of peroxidase labeled anti-mouse IgG goat sera previously diluted 10000 fold with Solution A and incubated at 37° C. for 1 hour, and washed. Then, each of wells was added with 100 µl of substrate solution (O-phenylenediamine: 40 mg, 20 µl of 30% hydrogen peroxide in 100 ml of citrate-sodium phosphate buffer) and kept at room temperature. Optical density at 492 nm of the wells was measured.

Amount of antibody was measured by calibration curve made by use of anti-ovalbumin mouse IgG antibody which was purified by ovalbumin bonded Sepharose® 4B (agarose gel) column affinity chromatography of antisera obtained from mice immunized with ovalbumin and Freund's complete adjuvant. The results of antibody measurement in the serum samples used in Example 9 were shown in Table 2.

TABLE 2

| Immunomodulator | Dose (%) | Animal group No. | Anti ovalbumin IgG (ng/ml) |
|---|---|---|---|
| Control | 0 | 1 | 300 |
| Heat killed cell | 0.01 | 2 | 310 |
| | 0.1 | 3 | 310 |
| | 1 | 4 | 640 |
| Enzymatically decomposed whole Cell (Example 4) | 0.01 | 5 | 285 |
| | 0.1 | 6 | 490 |
| | 1 | 7 | 1015 |
| Enzymatically decomposed active fraction (Example 3) | 0.001 | 8 | 300 |
| | 0.01 | 9 | 520 |
| | 0.1 | 10 | 1820 |
| | 1 | 11 | 1910 |

The result revealed that administration of bacterial cells of Corynebacterium glutamicum and also its enzymatically decomposed materials enhanced production of IgG antibody.

Example 11

Safety Studies on the Immunomodulator

Safety of immunomodulative decomposed material having suppressive ctivity on IgE antibody production.

As for single dose oral toxicity study, a group of 5 male rats of 4 weeks old SD strain was orally administered with enzymatically decomposed material prepared by the method described in Example 4 at a dose of 2 g/kg body weight. As for repeated oral toxicity, a group of 10 male rats of 4 weeks old SD strain was fed with food containing at a concentration of 5% for 4 weeks. Both groups of rats were compared with rats of respective control groups. There were no toxic signs after single oral dose of the test sample, and as shown in Table 3, there were no changes in increase in body weight and behavior between the test group and control.

TABLE 3

| Feed | Body weight (g) at beginning of feeding | Body weight (g) after 4 week feeding |
|---|---|---|
| 5% (w/w) enzymatically decomposed material (in Example 4) containing feed | 220.5 ± 10.6 | 401.4 ± 18.8 |
| Control | 222.8 ± 10.9 | 403.3 ± 21.8 |

Example 12

Table Type Food Containing the Immunomodulator

Ninety milligrams of immunomodulative decomposition material of Corynebacterium glutamicum bacterial cells using egg-white lysozyme and bromelain obtained in Example 4, 30 mg of starch, 180 mg of Avicell® (Cellulose) were mixed and a tablet-type food was produced in a usual manner such that one tablet was 300 mg.

Example 13

Drink Containing the Immunomodulator

Purified water was added to two parts of decomposition material of *Corynebacterium glutamicum* bacterial cells using egg-white lysozyme and bromelain obtained in Example 4, 10 parts of cocoa butter, 7 parts of granulated sugar, 7 parts of milk and 0.05 part of emulsifying agent to adjust the total amount to 100 parts, and a cocoa drink was produced in a usual manner.

Example 14

Tablet Type Food Containing the Immunomodulator

Ninety milligrams of enzymatically decomposed material of *Corynebacterium ammoniaphilum* bacterial cells using egg-white lysozyme and bromelain obtained in Example 8, 30 mg of starch, 180 mg of Avicell® (Cellulose, Asahi Chemical Industry Co., Ltd.) were mixed and a tablet-type food was produced in a usual manner such that one tablet was 300 mg.

Example 15

Drink Containing the Immunomodulator

Purified water was added to two parts of enzymatically decomposed material of *Corynebacterium ammoniaphilum* bacterial cells using egg-white lysozyme and bromelain obtained in Example 8, 10 parts of cocoa butter, 7 parts of granulated sugar, 7 parts of milk and 0.05 parts of emulsifying agent to adjust the total amount to 100 parts, and a cocoa drink was produced in a usual manner.

Example 16

Treatment of Allergic Disorders

Twenty-four patients, 18 to 47 years old, 16 males and 8 females, who suffered from pollinosis were divided into two groups consisting of 12 persons. A hundred gram of cocoa drink, obtained in Example 13, was daily given for 6 months in one group. The other group was served as a control. Every persons of both groups was admitted wearing a cotton mask and occasional intake of medicines prescribed by the doctors of the present clinical study. Allergic status was evaluated at every 2 months for each patient by the same doctor and scored symptoms about nasal, ocular, cutaneous, and respiratory signs. The scoring of the clinical features was normal (0), mild (1), moderate (2) and severe (3). Total IgE level in the serum obtained at the start and the end of the study were measured by RIST (radioimmunosorbent test) method.

The difference in the means of sum totals of clinical scoring between both groups was tested by one-tailed t-test. The differences of IgE levels during 6 months before and after the treatment was compared for each group by two-tailed t-test. Significance was accepted at $p<0.05$. The results were summarized in Table 4.

The number of clinical scoring in the group that ate the immunomodulator was significantly lower than that of the control group. IgE levels of this group was also significant decreased. However, no significant decrease in the IgE level of the control group was observed.

TABLE 4

| Patient No. | Treatment | Sum of score | IgE (IU/ml) Start | IgE (IU/ml) End |
|---|---|---|---|---|
| 1 | Yes | 32 | 7070 | 5960 |
| 2 | Yes | 20 | 380 | 390 |
| 3 | Yes | 16 | 2309 | 2005 |
| 4 | Yes | 22 | 130 | 100 |
| 5 | Yes | 29 | 2248 | 2255 |
| 6 | Yes | 12 | 174 | 105 |
| 7 | Yes | 18 | 770 | 780 |
| 8 | Yes | 30 | 1110 | 526 |
| 9 | Yes | 20 | 145 | 30 |
| 10 | Yes | 13 | 640 | 650 |
| 11 | Yes | 19 | 120 | 25 |
| 12 | Yes | 12 | 632 | 280 |
| Mean ± SD | | 20.3 ± 6.7** | 1310.7 ± 1968.3 | 1092.2 ± 1702.2* |
| 13 | No | 25 | 220 | 200 |
| 14 | No | 40 | 2100 | 1210 |
| 15 | No | 26 | 85 | 90 |
| 16 | No | 29 | 901 | 960 |
| 17 | No | 33 | 170 | 1900 |
| 18 | No | 38 | 1705 | 2185 |
| 19 | No | 38 | 88 | 204 |
| 20 | No | 20 | 260 | 130 |
| 21 | No | 28 | 8000 | 8226 |
| 22 | No | 22 | 68 | 130 |
| 23 | No | 32 | 5010 | 3480 |
| 24 | No | 28 | 205 | 201 |
| Mean ± SD | | 29.9 ± 6.2 | 1567.7 ± 2485.3 | 1576.3 ± 2352.8 |

**$p < 0.01$ between treated and control groups.
*$p < 0.05$ between IgE levels during 6 months before and after the treatment.

What is claimed is:

1. A method of treating pollinosis, comprising orally administering to a person who has the pollinosis, a pharmacologically effective amount of an isolated Corynebacterial cell wall decomposition product obtained by dissolving the cell wall of *Corynebacterlum glutamicum* with one of glucosidase and endopeptidase in an isotonic solution medium, separating protoplasts generated by the dissolution of the cell wall from the medium and enzymatically treating the dissolved cell wall with the other of endopeptidase and glucosidase.

2. A method of treating pollinosis in a person comprising orally administering to the person a pharmaceutically effective amount of an isolated cell wall decomposition product obtained by enzymatically dissolving the cell wall of *Corynebacterium glutamicum*.

* * * * *